United States Patent [19]
Prasad

[11] Patent Number: 5,846,944
[45] Date of Patent: Dec. 8, 1998

[54] PURIFIED SDG AS AN ANTIOXIDANT

[75] Inventor: Kailash Prasad, Saskatoon, Canada

[73] Assignee: The University of Saskatchewan, Saskatoon, Canada

[21] Appl. No.: 826,500

[22] Filed: Apr. 3, 1997

[51] Int. Cl.$^6$ .................................................. A61K 31/70
[52] U.S. Cl. ........................................... 514/25; 536/18.1
[58] Field of Search ............................... 514/25; 536/18.1

[56] References Cited

U.S. PATENT DOCUMENTS

| | | | |
|---|---|---|---|
| 5,340,742 | 8/1994 | Barclay | 435/256.8 |
| 5,518,918 | 5/1996 | Barclay | 435/257.1 |

FOREIGN PATENT DOCUMENTS

| | | |
|---|---|---|
| 9408467 | 4/1994 | WIPO . |
| 9630468 | 10/1996 | WIPO . |

OTHER PUBLICATIONS

Bakke, JE and Klosterman, HJ: "A New Diglucoside From Flaxseed" *Proc. North Dakota Acad. Sci. 10*, 18–22, 1956.

Klosterman, HJ and Smith, F: "The Isolation of β–Hydroxy–β–Methylglutaric Acid From the Seed of Flax", *J. Am. Chem. Soc. 76*, 1229–1230, (Mar. 5, 1954).

MacRae, WD and Towers, GHN: "Biological Activities of Lignans", *Phytochemistry*, vol. 23, No. 6, pp. 1207–1220, 1984.

Harris, RK and Haggerty, WJ: "Assays for Potentially Anticarcinogenic Phytochemicals in Flaxseed", *Cereal Foods World*, vol. 38, No. 3, pp. 147–151, (Mar. 1993).

Bambagiotti–Alberti, M et al.,: "Revealing the Mammalian Lignan Precursor Secoisolariciresinol Diglucoside in Flax Seed by Ionspray Mass Spectometry", *Rapid Communications in Mass Spectometry*, vol. 8, pp. 595–598, 1994.

Obermeyer, WR et al.,: "Chemical Studies of Phytoestrogens in Flas and Chaparral", *Society for Experimental Biology and Medicine*, pp. 6–12, 1995.

Ratnayake et al., "Chemical and Nutritional Studies of Flaxseed (Variety Linott) in Rats," *J. Nutritional Biochemistry*, 3, 232–240 (May 1992).

Thompson et al., "Flaxseed and Its Lignan and Oil Components Reduce Mammary Tumor Growth at a Late Stage of Carcinogenesis," *Carcinogenesis*, 17(6), 1371–1376 (1996).

Clark et al., "Omega–3 Fatty Acid Supplementation in Clinical and Experimental Lupus Nephritis," part of Proceedings From The National Kidney Foundation Annual Meeting—Symposium on Essential Fatty Acid Deficiencies and ω–3 Unsaturated Fat Dietary Supplementation in Glomerulonephritis: Basis and Practice Baltimore, Md, Nov. 11–15, 1992; *American J. of Kidney Diseases*, 23(5), 644–647 (May 1994).

Kelley et al., "Dietary α–Linolenic Acid Alters Tissue Fatty Acid Composition, But Not Blood Lipids, Lipoproteins or Coagulation Status in Humans," *Lipids*, 28(6), 533–538 (Jun. 1993).

Bierenbaum et al., "Reduced Atherogenic Risk in Hyperlipemic Humans with Flax Seed Supplementation: A Preliminary Report," *J. Amer. College of Nutrition*, 12(5), 501–504 (Oct. 1993).

Cunnane et al., "High α–Linolenic Acid Flaxseed (*Linum usitatissimum*): Some Nutritional Properties in Humans," *British J. of Nutrition*, 69, 443–453 (1993).

Ranhotra et al., "Lipidemic Response in Rats Fed Flaxseed Oil and Meal," *Cereal Chemistry*, 70(3), 364–366 (1993).

Jenab et al., "The Influence of Flaxseed and Lignans on Colon Carcinogenesis and β–Glucuronidase Activity," *Carcinogenesis*, 17(6), 1343–1348 (1996).

Bambagiotti–Albert et al., "Investigation of Mammalian Lignan Precursors in Flax Seed: First Evidence of Secoisolariciresinol Diglucoside in Two Isomeric Forms by Liquid Chromatography/Mass Spectrometry," *Rapid Comm. Mass Spectrometry*, 8(12), 929–932 (1994).

*Primary Examiner*—Douglas Robinson
*Assistant Examiner*—I. Eric Crane

[57] ABSTRACT

The compound secoisolariciresinal diglucoside (SDG), obtained from flaxseed is used for reducing or preventing the development of hypercholesterolemic atherosclerosis and for reducing total cholesterol in humans or animals. It is also used for treating diabetes mellitus.

12 Claims, 3 Drawing Sheets

PURIFIED SDG AS AN ANTIOXIDANT

BACKGROUND OF THE INVENTION

This invention relates to a method for the use of purified SDG (secoisolariciresinol diglucoside) for the treatment of atherosclerosis e.g., reducing or preventing the development of hypercholesterolemic atherosclerosis and for reducing total cholesterol. It is also useful for the treatment of diabetes mellitus.

Atherosclerosis remains the single most important etiology of cardiovascular morbidity and mortality in North America, with the principal distribution among symptomatic patients being approximately 7 million cardiacs, 3 million peripheral vascular disease sufferers and 750,000 stroke victims. An additional 6.5 million patients are affected by diabetic vascular disease. Approximately 1 million surgeries are performed annually for vascular disease with cardiacs accounting from some 60% of the total. The current therapies for cardiovascular diseases, particularly in symptomatic patients, include limiting the progression of the disease through control of the patient's environmental factors, reducing stress by lifestyle modification, weight reduction where appropriate and through a combination of more intensive medical and surgical treatments.

Pharmacological approaches have focused on such aspects as lowering the level of serum lipids, on anticoagulation and on the control of hypertension and of diabetes. Both surgical and medical modalities, uses to treat symptomatic patients, have limited applicability since the underlying condition is end stage atherosclerosis. The evolution of this end stage condition appears to result from changes in luminal and transmural arterial wall characteristics, including the progressive narrowing in luminal diameter.

Current therapies of cardiovascular disease and in particular atherosclerosis do not treat the cause of the disease, but instead treat the symptoms or lower the risk factors associated with the disease. Pharmacological agents prescribed for these conditions include lipid lowering agents such as lovastatin, probucol, nicotinic acid and colestipol, aspirin, angiotensin converting enzyme inhibitors, beta-adrenergic blocker etc. These agents are not selective, affect other organs, have significant side effects and as a result, may be far from being cost effective. Given that cardiovascular diseases are the leading cause of death and disability in the world and that 90% of cardiovascular disease is presently diagnosed as atherosclerotic, there is a strong need to identify new methods and pharmacological agents, particularly of plant origins, for their treatment.

The literature describes the use of whole flaxmeal as a potential agent for the control of a range of disorders, including breast cancer, colon cancer, and Lupus. Researchers have also inferred a role for flax as a means of reducing the size of cancerous nodes in mice afflicted with breast cancer. Whole flaxseed has also been observed to have beneficial effects on cholesterol metabolism in animals where the beneficial effects were attributed to the oil fraction, and to affect blood glucose levels, where the beneficial effect was attributed to the mucilage. Whole flaxseed has also been shown to have a beneficial effect on human blood cholesterol levels. Several health food publications where uses of flax for purposes such as cholesterol reduction have been considered, improved Taxation and the lowering of blood pressure have been implied.

Flaxseed is known to contain a myriad of small organic molecules, mostly resulting from the metabolic pool during the formation of the seed as part of normal plant growth. One of these is secoisolariciresinol diglucoside (SDG) an entity from the collective chemical family referred to as plant lignans. SDG was first reported in the scientific literature by Bakke and Klosterman (1956) A New Diglucoside From Flaxseed, *Proceedings of the North Dakota Academy of Science* 10:18–22. It has been the subject of a number of laboratory studies; the SDG used in these studies has been prepared in the laboratory by methods unsuited to commercial practice.

Although the consumption of whole ground flaxmeal may offer some potential for the control or alleviation of certain medical disorders, a major drawback lies in the fact that only up to 30–45 g of this product can be consumed on a daily basis. The limitation is due to some readily apparent side effects such as increased Taxation, believed due to the presence of a mucilaginous substance, and also to progressive weight gain resulting from the rather high caloric value of the oil component. Flax contains upwards of 40% oil. The use of whole ground flaxseed or meal is also restricted in part because of the presence of cyanogenic glycosides present in the seed.

In Westcott and Muir, U.S. patent application Ser. No. 08/415,050, filed Mar. 31, 1995, there is described a practical method of extracting and purifying SDG, the principal lignan from flax. By this technique, SDG can be obtained in a purity of greater than 95%.

The purpose of the present invention is to provide a method of using flaxseed for medical purposes without the aforementioned drawbacks of Taxation, cyanogenic glycosides, and caloric loads.

SUMMARY OF THE INVENTION

In accordance with this invention, it has been found that by administering secoisolariciresinol diglucoside (SDG) from flaxseed in substantially pure form to a human or non-human animal, development of hypercholesterolemic atherosclerosis can be prevented together with a reduction in total cholesterol. Also, SDG is useful for the treatment of diabetes mellitus. This is achieved without the undesirable side effects of Taxation, cyanogenic glycosides and caloric loads.

The SDG is preferably used at a high degree of purity of over 90%, with a purity of over 95% being the preferred. However, it may also be used in the form of a crude extract of lower purity, e.g. 85% purity. It can be administered orally or intravenously, and has been found to be highly effective when administered in a once daily oral dosage of 5–20 mg per kg of body weight. The oral doses may conveniently be in the form of tablets or capsules and the SDG may be used together with a variety of pharmaceutically acceptable diluents or carriers.

DESCRIPTION OF THE PREFERRED EMBODIMENTS

Figure 1:
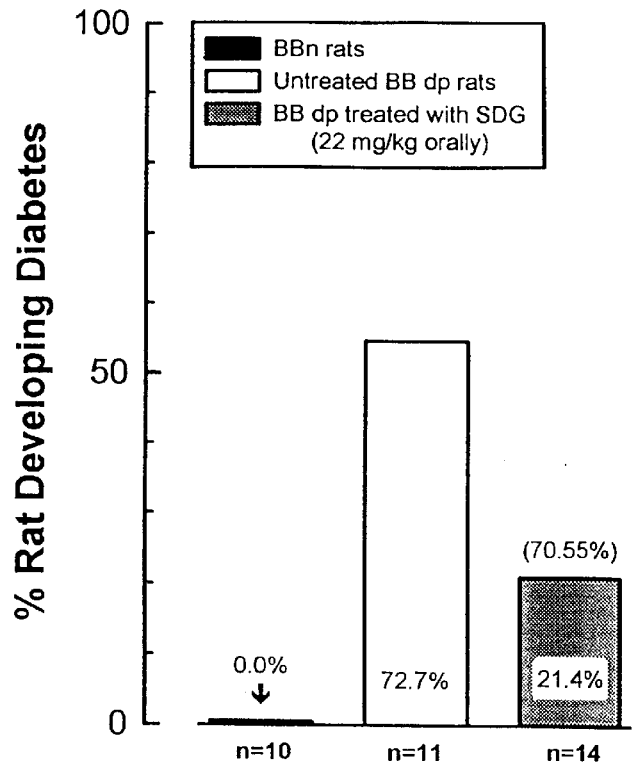
FIG. 1 is a bar graph showing percentage of rats developing diabetes mellitus.

The invention is further illustrated by the following non-limiting Examples.

Example 1

Experimental Protocol

Experiments were carried out on six to eight week old female New Zealand white rabbits weighing between 1.8 and 2.0 kg. The rabbits were divided into seven groups as shown in Table 1. All procedures relating to the care and welfare of test animals within this experimental protocol conformed to a Standard Operating Procedure (SOP) approved by the Council on Animal Care, University of Saskatchewan, Saskatoon, Saskatchewan, Canada.

Blood samples for measurement of triglycerides (TG), total cholesterol (TC), low density lipoprotein cholesterol (LDL-C), very-low density lipoprotein cholesterol (VLDL-C), and high density lipoprotein cholesterol (HDL-C) were taken before the animals were assigned to the experimental diet (T=0), and after 1 (T=1) and 2 months (T=2) on the experimental diet. The rabbits were sacrificed under pentabarbital anesthesia at the end of 2 months. The aorta was removed for the assessment of atherosclerotic plaques.

TABLE 1

Experimental Diet Groups

| Group | Diet |
|---|---|
| Control (n = 8) | Rabbit Chow Diet |
| 1% Cholesterol (n = 6) | Rabbit Chow + 1% Cholesterol |
| Flax Type I control (n = 8) | Rabbit Chow + 15% Type I flaxseed |
| Flax Type I + 1% Cholesterol (n = 8) | Rabbit Chow 15% Type I flaxseed + 1% Cholesterol |
| Flax Type II control (n = 5) | Rabbit Chow + 15% Type II flaxseed |
| Flax Type II + 1% Cholesterol (n = 5) | Rabbit Chow + 15% Type II flaxseed + 1% Cholesterol |
| SDG Control (n = 5) | Rabbit Chow + 15mg/kg SDG (Oral dose) |
| SDG + 1% Cholesterol (n = 5) | Rabbit Chow + 15mg/kg SDG (Oral dose) + 1% Cholesterol |

Number in parenthesis indicates the number of rabbits in each group.

Much has been made of the importance of the composition of certain dietary fats toward health, particularly in relation to the degree of saturation of the fatty acid composition of the triglycerides. In this example, 2 varieties of flax was used, of similar total oil content (35%) but differing in the level of the principal triglyceride fatty acid, alpha-linolenic acid. Type I flax had 55% alpha-linolenic acid while Type II had only 2–3 %. The major triglyceride fatty acid in Type II flaxseed was linoleic acid. The dosage of whole ground flax was 15% in the diets of the test animals. Both Type I and Type II flax were of the brown seed type and both flax types contained similar concentrations of the lignan SDG.

The SDG was obtained from Agriculture and Agri-Food Canada and was extracted from flaxseed by the method described in U.S. application Ser. No. 08/415,050, filed Mar. 31, 1995, incorporated herein by reference.

The results obtained are shown in the following Tables 2 to 8.

TABLE 2

Effect of diet on the development of Atherosclerotic Plaques in New Zealand White Rabbits

| Group | Atherosclerotic plaques (% of total internal surface area) | % Inhibition of Atherosclerotic Development |
|---|---|---|
| Control (n = 8) | 0 | — |
| 1% Cholesterol (n = 6) | 78.97 ± 5.44 | — |
| Flax Type I control (n = 8) | 0 | — |
| Flax Type I + 1% Cholesterol (n = 8) | 42.64 ± 7.82 | 46 |
| Flax Type II control (n = 5) | 0 | — |
| Flax Type II + 1% Cholesterol (n = 5) | 24.64 ± 7.02 | 69 |
| SDG Control (n = 5) | 0 | — |
| SDG + 1% Cholesterol (n = 5) | 21.69 ± 2.06 | 73 |

TABLE 3

Total serum cholesterol levels (mmol/L) in rabbits

| Group | 0 month | 1 month | 2 months |
|---|---|---|---|
| Control (n = 8) | 2.26 ± 0.20 | 1.90 ± 0.23 | 1.74 ± 0.29 |
| 1% Cholesterol (n = 6) | 2.68 ± 0.20 | 78.00 ± 4.08 | 67.80 ± 7.80 |
| Flax Type I control (n = 8) | 1.65 ± 0.21 | 2.53 ± 0.27 | 4.63 ± 0.89 |
| Flax Type I + 1% Cholesterol (n = 8) | 2.43 ± 0.19 | 82.69 ± 3.41 | 84.00 ± 6.04 |
| Flax Type II control (n = 5) | 1.78 ± 0.11 | 1.96 ± 0.09 | 2.64 ± 0.68 |
| Flax Type II + 1% Cholesterol (n = 5) | 1.59 ± 0.12 | 54.50 ± 5.66 | 58.63 ± 7.99 |
| SDG Control (n = 5) | 1.42 ± 0.11 | 1.22 ± 0.11 | 1.12 ± 0.10 |
| SDG + 1% Cholesterol (n = 5) | 2.26 ± 0.25 | 68.20 ± 7.41 | 45.18 ± 6.68 |

TABLE 4

Serum LDL-C levels (mmol/L) in rabbits

| Group | 0 month | 1 month | 2 months |
|---|---|---|---|
| Control (n = 8) | 0.90 ± 0.10 | 0.93 ± 0.22 | 1.03 ± 0.27 |
| 1% Cholesterol (n = 6) | 1.22 ± 0.17 | 76.86 ± 4.06 | 66.49 ± 7.50 |
| Flax Type I control (n = 8) | 0.59 ± 0.19 | 1.26 ± 0.13 | 2.90 ± 0.65 |
| Flax Type I + 1% Cholesterol (n = 8) | 1.21 ± 0.24 | 81.40 ± 3.40 | 82.55 ± 6.04 |
| Flax Type II control (n = 5) | 0.73 ± 0.14 | 0.79 ± 0.09 | 1.33 ± 0.61 |
| Flax Type II + 1% Cholesterol (n = 5) | 0.57 ± 0.08 | 52.56 ± 5.51 | 55.38 ± 7.70 |
| SDG Control (n = 5) | 0.34 ± 0.09 | 0.33 ± 0.06 | 0.25 ± 0.04 |
| SDG + 1% Cholesterol (n = 5) | 1.09 ± 0.19 | 66.26 ± 7.23 | 43.25 ± 6.64 |

TABLE 5

Serum VLDL-C levels (mmol/L) in rabbits

| Group | 0 month | 1 month | 2 months |
|---|---|---|---|
| Control (n = 8) | 0.50 ± 0.05 | 0.27 ± 0.04 | 0.31 ± 0.03 |
| 1% Cholesterol (n = 6) | 0.74 ± 0.06 | 0.65 ± 0.07 | 0.47 ± 0.06 |
| Flax Type I control (n = 8) | 0.56 ± 0.07 | 0.61 ± 0.06 | 0.66 ± 0.13 |
| Flax Type I + 1% Cholesterol (n = 8) | 0.59 ± 0.10 | 0.79 ± 0.09 | 0.80 ± 0.14 |
| Flax Type II | 0.41 ± 0.03 | 0.31 ± 0.07 | 0.39 ± 0.11 |

TABLE 5-continued

Serum VLDL-C levels (mmol/L) in rabbits

| Group | 0 month | 1 month | 2 months |
|---|---|---|---|
| control (n = 5) | | | |
| Flax Type II + 1% Cholesterol (n = 5) | 0.65 ± 0.05 | 1.44 ± 0.24 | 2.75 ± 0.55 |
| SDG Control (n = 5) | 0.50 ± 0.06 | 0.29 ± 0.01 | 0.27 ± 0.02 |
| SDG + 1% Cholesterol (n = 5) | 0.55 ± 0.04 | 0.64 ± 0.08 | 0.83 ± 0.16 |

TABLE 6

Serum HDL-C levels (mmol/L) in rabbits

| Group | 0 month | 1 month | 2 months |
|---|---|---|---|
| Control (n = 8) | 0.67 ± 0.04 | 0.70 ± 0.04 | 0.62 ± 0.09 |
| 1% Cholesterol (n = 6) | 0.72 ± 0.07 | 0.50 ± 0.00 | 0.50 ± 0.00 |
| Flax Type I control (n = 8) | 0.50 ± 0.08 | 0.79 ± 0.09 | 0.50 ± 0.00 |
| Flax Type I + 1% Cholesterol (n = 8) | 0.65 ± 0.06 | 0.50 ± 0.00 | 0.50 ± 0.00 |
| Flax Type II control (n = 5) | 0.64 ± 0.02 | 0.86 ± 0.09 | 0.92 ± 0.06 |
| Flax Type II + 1% Cholesterol (n = 5) | 0.46 ± 0.03 | 0.50 ± 0.00 | 0.50 ± 0.00 |
| SDG Control (n = 5) | 0.58 ± 0.09 | 0.60 ± 0.06 | 0.50 ± 0.00 |
| SDG + 1% Cholesterol (n = 5) | 0.62 ± 0.10 | 1.30 ± 0.18 | 1.20 ± 0.48 |

TABLE 7

Serum Triglyceride levels (mmol/L) in rabbits

| Group | 0 month | 1 month | 2 months |
|---|---|---|---|
| Control (n = 8) | 1.11 ± 0.11 | 0.61 ± 0.08 | 0.68 ± 0.06 |
| 1% Cholesterol (n = 6) | 1.63 ± 0.12 | 1.42 ± 0.15 | 1.68 ± 0.65 |
| Flax Type I control (n = 8) | 1.23 ± 0.15 | 1.35 ± 0.14 | 1.39 ± 0.26 |
| Flax Type I + 1% Cholesterol (n = 8) | 1.25 ± 0.20 | 1.74 ± 0.21 | 1.75 ± 0.31 |
| Flax Type II control (n = 5) | 0.91 ± 0.08 | 0.69 ± 0.13 | 0.87 ± 0.24 |
| Flax Type II + 1% Cholesterol (n = 5) | 1.43 ± 0.10 | 3.16 ± 0.52 | 4.32 ± 0.58 |
| SDG Control (n = 5) | 1.10 ± 0.13 | 0.63 ± 0.02 | 0.60 ± 0.12 |
| SDG + 1% Cholesterol (n = 5) | 1.21 ± 0.09 | 1.40 ± 0.17 | 1.83 ± 0.35 |

TABLE 8

Body weight (kg) of hypercholesterolemic rabbits

| Group | 0 month | 1 month | 2 months |
|---|---|---|---|
| Control (n = 8) | 1.55 ± 0.06 | 2.99 ± 0.14 | 3.73 ± 0.26 |
| 1% Cholesterol (n = 6) | 1.51 ± 0.09 | 2.56 ± 0.12 | 2.94 ± 0.06 |
| Flax Type I control (n = 8) | 1.32 ± 0.05 | 2.26 ± 0.07 | 3.03 ± 0.11 |
| Flax Type I + 1% Cholesterol (n = 8) | 1.79 ± 0.09 | 2.58 ± 0.10 | 2.84 ± 0.08 |
| Flax Type II control (n = 5) | 1.13 ± 0.03 | 2.24 ± 0.05 | 2.84 ± 0.07 |
| Flax Type II + 1% Cholesterol (n = 5) | 1.39 ± 0.04 | 2.48 ± 0.12 | 2.84 ± 0.10 |
| SDG Control (n = 5) | 1.75 ± 0.02 | 2.34 ± 0.04 | 2.84 ± 0.05 |
| SDG + 1% Cholesterol (n = 5) | 1.25 ± 0.03 | 1.98 ± 0.08 | 2.35 ± 0.10 |

The effectiveness of SDG can be compared to a number of other compounds that have been shown to have anti-atherosclerotic pharmacological effects in New Zealand White rabbits, including Probucol, and Vitamin E. Probucol at a dosage rate of 0.5% in the diet (equivalent to 250 mg/Kg body weight) in a 0.5% cholesterol diet, reduced the hypercholesterolemic atherosclerosis by up to 43%, but did not reduce the total cholesterol in the bloodstream. The effect of Probucol on reducing atherosclerosis varied between 15–45%, depending upon the extent of the hypercholesterolemia.

In studies with Vitamin E, a known and accepted antioxidant, recommended for promoting healthy heart function, Vitamin E (40 mg/kg) reduced hypercholesterolemic atherosclerosis in rabbits by up to 73%, without reducing the total blood cholesterol, whereas SDG accomplishes both. The mechanism of action for Vitamin E is now generally accepted as preventing the development of hypercholesterolemic atherosclerosis through its antioxidant activity and its ability to scavenge free radicals in the bloodstream.

Example 2

The effects of SDG on the endotoxic-shock-induced changes in the cardiovascular function and contractility, and on lipid peroxidation product malondialdehyde (MDA) a measure of levels of oxygen free radicals (OFR), and antioxidant reserve of the myocardium were investigated in anesthetized dogs. The dogs were divided into three groups. Group I, (sham 3 hours, n=5). Group II, (ET, n=9), these dogs received endotoxin (5 mg/kg, intravenously). Group III (SDG+ET) similar to Group II, except that this group of dogs received SDG (10 mg/kg intravenously) 15 min prior to administration of endotoxin. Mean aortic blood pressure (mAo), cardiac index (CI) a measure of cardiac function, and cardiac contractility (dp/dt at CPIP/PAW) were measured before (0 min) and at 30 min, 60 min, 90 min, 120 min and 180 min after endotoxin administration. At the end of 3 hours of experiment heart was removed for measurement of MDA and antioxidant reserve. Cardiac function and contractility were measured. Left ventricular MDA (LV-MDA) and left ventricular chemiluminescence (LV-CL) a measure of antioxidant reserve were also estimated.

The mAo remained unchanged in the sham group at an average of about 133 mm Hg but decreased significantly to about 85 mm Hg in the ET-shock group. SDG prevented the ET-induced fall in mAO up to 30 min. Endotoxin produced a marked fall in cardiac index from about 4 to about 2 l.min.m$^{-2}$ while SDG prevented the ET-induced fall in cardiac index. Index of myocardial contractility quickly decreased from about 100 to about 50 dp/dt at CPIP/PAW (% of initial values) in ET-treated dogs and SDG prevented any ET-induced decrease in index of myocardial contractility. Left ventricular MDA (LV-MDA) increased in the ET-shock group while SDG prevented the ET-induced increase in LV-MDA. LV-CL increased in the ET-treated group from about 10,000 to about 15,000 mv.sec/mg protein suggesting a decrease in the antioxidant reserve. SDG prevented the ET-induced decrease in antioxidant reserve.

These results indicate that endotoxic shock induced depression of mean aortic pressure, cardiac function and contractility were associated with an increase in the levels of oxygen free radicals and a decrease in the antioxidant reserve. SDG prevented the endotoxin-induced depression of the mean aortic pressure, cardiac function and contractility and these changes were associated with a decrease in the levels of oxygen free radicals and an increase in antioxidant reserve. These results indicate that SDG prevented the ET-shock-induced depression of cardiac function and contractility and that the protective effect of SDG against endotoxic shock could be due to antioxidant activity of SDG.

Example 3

Effects of SDG were investigated on the experimental diabetes in rats. Experimental diabetes mellitus was produced in Sprague-Dawley rats by injecting streptozotocin (STZ, 65 mg/kg) intravenously. Diagnosis of diabetes mellitus was established by testing for the presence of glucosuria with Ames Multi Stix (Miles Canada Inc., Etobicoke, Ontario) on the 3rd day after streptozotocin administration. The rats were divided into 4 groups. Group I, control; Group II (STZ) this group received streptozotocin treatment for; Group III [SDG (22 mg/kg)+STZ], this group received SDG (22 mg/kg orally in drinking water) 3 days prior to STZ administration and for another 3 weeks after confirmation of diabetes mellitus which was done 3 days after STZ administration. Group IV [SDG (44 mg/kg)+STZ], similar to Group III except the dose of SDG was 44 mg/kg.

The results are summarized in Table 9. Streptozotocin administration produced diabetes mellitus in 75% of the rats and the plasma glucose at the end of three weeks were very high in the diabetic group as compared control. 25% of rats which did not develop diabetes had plasma glucose levels of 6.12 mmoles/liter. SDG in the dose of 44 mg/kg was more effective than in the dose of 22 mg/kg in preventing the development of diabetes and the plasma levels of glucose were similar in the two groups. Plasma glucose levels were similar in SDG-treated groups and were much lower than those in streptozotocin-treated group. These results suggest that SDG prevented the development of STZ-induced diabetes mellitus by approximately 81%.

TABLE 9

Effects of SDG on streptozotocin-induced diabetes mellitus in rats.

| Groups | # Rats/ Group | # Rats Developing Diabetes | Plasma Glucose (mmoles/litre) |
|---|---|---|---|
| Group I: Control | 16 | 0 | 6.4 ± 0.31 |
| Group II: STZ | 8 | 6 (75%) | 27.52 ± 0.79* |
| Group III: SDG (22 mg/kg) for 3 days + STZ | 12 | 2 (16.6%) | 9.63 ± 0.71*† |
| Group IV: SDG (44 mg/kg) for 3 days + STZ | 10 | 1 (10%) | 10.01 ± 0.76*† |

The plasma glucose levels are expressed as mean + S.E. The number in parenthesis indicate the percent of rats developing diabetes mellitus.
*P<0.05, Group I Vs other groups.
†P<0.05, Group II Vs Groups III and IV.

Example 4

The experiments of Example 1 were repeated using a different group of rabbits and different dosages of SDG. One series of tests were conducted in which SDG in pure form was administered orally in a daily dosage of 5 mg/kg. Another series of tests were conducted in which the SDG was in the form of a crude extract containing 89% by weight of SDG as obtained by the process described in U.S. application Ser. No. 08/415,050.

Testing was carried out in the same manner as in Example 1 and the results obtained are shown in the following Tables 10–17.

TABLE 10

Experimental Diet Groups

| | |
|---|---|
| 1% Cholesterol (n = 6) | Rabbit chow + 1% cholesterol |
| SDG (5 mg/kg) + 1% cholesterol (n = 7) | Rabbit chow + SDG (5 mg/kg, orally daily) + 1% cholesterol |
| SDG (89% pure) + 1% cholesterol (n = 5) | Rabbit chow + SDG (89% pure) [11.24 mg/kg, orally daily] + 1% cholesterol |

TABLE 11

Effect of diet on the development of Atherosclerotic plaques in New Zealand White Rabbits

| Group | Atherosclerotic plaques (% of total intimal surface area) | % Inhibition of Atherosclerotic Development |
|---|---|---|
| 1% Cholesterol (n = 6) | 73.18 | 0 |
| SDG (5 mg/kg) + 1% cholesterol (n = 7) | 47.57 | 35 |
| SDG (89% pure) (11.24 mg/kg) + 1% cholesterol (n = 5) | 38.10 | 48 |

TABLE 12

Effect of diet on total serum cholesterol levels (mmol/L) in New Zealand White Rabbits

| | Time (months) | | |
|---|---|---|---|
| Groups | 0 | 1 | 2 |
| 1% Cholesterol (n = 6) | 2.46 ± 0.41 | 54.08 ± 3.00 | 63.59 ± 5.46 |
| SDG (5 mg/kg) + 1% cholesterol (n = 7) | 2.31 ± 0.19 | 77.24 ± 7.22 | 59.61 ± 9.8 |
| SDG (89% pure) (11.24 mg/kg) + 1% cholesterol (n = 5) | 1.55 ± 0.14 | 69.38 ± 3.68 | 62.01 ± 4.65 |

TABLE 13

Effect of diet on serum LDL-C levels (mmol/L) in New Zealand White Rabbits

| | Time (months) | | |
|---|---|---|---|
| Groups | 0 | 1 | 2 |
| 1% Cholesterol (n = 6) | 1.11 ± 0.40 | 48.77 ± 2.37 | 62.34 ± 5.24 |
| SDG (5 mg/kg) + 1% cholesterol (n = 7) | 0.89 ± 0.14 | 75.98 ± 9.04 | 58.68 ± 9.69 |
| SDG (89% pure) (1 1.24 mg/kg) + 1% cholesterol (n = 5) | 0.59 ± 0.11 | 68.43 ± 3.65 | 60.83 ± 4.49 |

TABLE 14

Effect of diet on serum VLDL-C levels (mmol/L) in New Zealand White Rabbits

| | Time (months) | | |
|---|---|---|---|
| Groups | 0 | 1 | 2 |
| 1% Cholesterol (n = 6) | 0.57 ± 0.04 | 0.39 ± 0.08 | 0.73 ± 0.21 |
| SDG (5 mg/kg) + 1% cholesterol (n = 7) | 0.59 ± 0.09 | 0.44 ± 0.08 | 0.39 ± 0.09 |
| SDG (89% pure) (11.24 mg/kg) | 0.40 ± 0.04 | 0.45 ± 0.07 | 0.45 ± 0.13 |

TABLE 14-continued

Effect of diet on serum VLDL-C levels (mmol/L) in New Zealand White Rabbits

| Groups | Time (months) | | |
|---|---|---|---|
| | 0 | 1 | 2 |
| mg/kg) + 1% cholesterol (n = 5) | | | |

TABLE 15

Effect of diet on serum HDL-C levels (mmol/L) in New Zealand White Rabbits

| Groups | Time (months) | | |
|---|---|---|---|
| | 0 | 1 | 2 |
| 1% Cholesterol (n = 6) | 0.79 ± 0.10 | 0.90 ± 0.04 | 0.52 ± 0.09 |
| SDG (5 mg/kg) + 1% cholesterol (n = 7) | 0.83 ± 0.08 | 0.76 ± 0.42 | 0.48 ± 0.10 |
| SDG (89% pure) (11.24 mg/kg) + 1% cholesterol (n = 5) | 0.56 ± 0.06 | 0.53 ± 0.09 | 0.75 ± 0.10 |

TABLE 16

Effect of diet on serum triglyceride levels (mmol/L) in New Zealand White Rabbits

| Groups | Time (months) | | |
|---|---|---|---|
| | 0 | 1 | 2 |
| 1% Cholesterol (n = 6) | 1.25 ± 0.10 | 0.87 ± 018 | 1.60 ± 0.48 |
| SDG (5 mg/kg) + 1% cholesterol (n = 7) | 1.30 ± 0.19 | 0.97 ± 0.16 | 0.87 ± 0.20 |
| SDG (89% pure) (11.24 mg/kg) + 1% cholesterol (n = 5) | 0.88 ± 0.09 | 0.92 ± 0.09 | 0.94 ± 0.23 |

TABLE 17

Effect of diet on body weight (kg) of hypercholesterolemic New Zealand White Rabbits

| Groups | Time (months) | | |
|---|---|---|---|
| | 0 | 1 | 2 |
| 1% Cholesterol (n = 6) | 1.38 ± 0.03 | 2.33 ± 0.09 | 2.42 ± 0.13 |
| SDG (5 mg/kg) + 1% cholesterol (n = 7) | 1.47 ± 0.02 | 2.45 ± 0.04 | 2.58 ± 0.08 |
| SDG (89% pure) (11.24 mg/kg) + 1% cholesterol (n = 5) | 1.75 ± 0.08 | 2.57 ± 0.15 | 2.77 ± 0.13 |

Example 5

Studies were made to determine the effects of SDG on insulin dependent diabetes mellitus (IDDM, Type I) and non-insulin dependent diabetes mellitus (NIDDM, Type II) in rats. Two animal models of IDDM used were: streptozotocin-induced and diabetic prone (dp) BB rats (BBdp). The Zucker diabetic fatty rat (ZDF), an animal model closely resembling human NIDDM, was used for NIDDM.

Spontenaously Developing IDDM rats (BBdp rats)

BBdp rats develop diabetes melliuts spontaneously. Effects of SDG were investigated in BBdp rats to determine if SDG can prevent/retard the development/progression of diabetes mellitus, and if the diabetes is associated with oxidative stress in this strain of rats. Serum malondialdehyde (MDA) a measure of levels of oxygen radicals, and antioxidant reserve [pancreatic-chemiluminescence (Pancreatic-CL)] were assessed in blood and pancreas. Male 35-day old BBdp and age matched nondiabetic prone BE (BBn) rats were obtained from Animal Resources Division, Health Protection Branch (Ottawa, Canada).

Two rats from BBn and 4 rats from BBdp at the age of 35 days were sacrificed to measure serum glucose and MDA, and pancreatic MDA and antioxidant reserve. The remaining rats were assigned to 3 groups: Group I, Control (BBn) (n=10); Group II, BBdp-untreated (n=11); Group III, BBdp-treated with SDG (22 mg/kg daily, orally in drinking water) (n=14). Diagnosis of diabetes mellitus was established by testing for the presence of glucosuria which was done every altenate day for 120 days or until glucosuria appeared. Once they developed diabetes or at the end of 120 days rats were anesthetized with nembutal sodium. Blood samples were taken to measure serum glucose and MDA, and pancreas were removed to assess pancreatic MDA and antioxidant reserve. None of the BBdp rats tested positive for glucosuria at 5 weeks and at that age the serum glucose in BBn and BBdp rats were 8.75±0.63 and 10.03±0.65 mmoles/L respectively.

The results are summarized in FIGS. 1–5.

FIG. 1 shows the percentage of BBdp rats with or without SDG treatment developing diabetes mellitus, with n being the number of rats in each group. The numbers in parenthesis indicate the percentage of prevention of developing diabetes mellitus by SDG. The control (BBn) rats did not develop diabetes.

Figure 2:
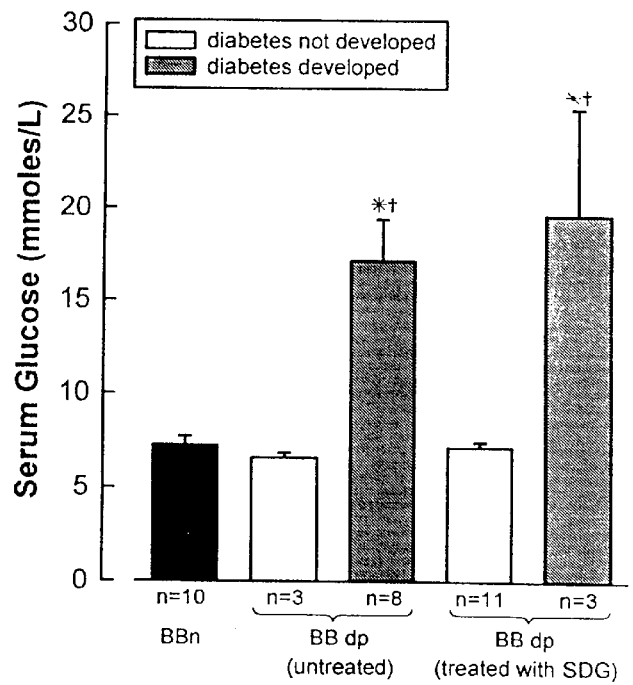
FIG. 2 is a bar graph showing serum glucose levels in three experimental groups.

FIG. 2 shows the serum glucose levels in the experimental groups, with the results being expressed as mean±SE.

*$p<0.05$, different from control (BBn) rats.

†$p<0.05$, different from nondiabetic rats within each treatment.

Figure 3:
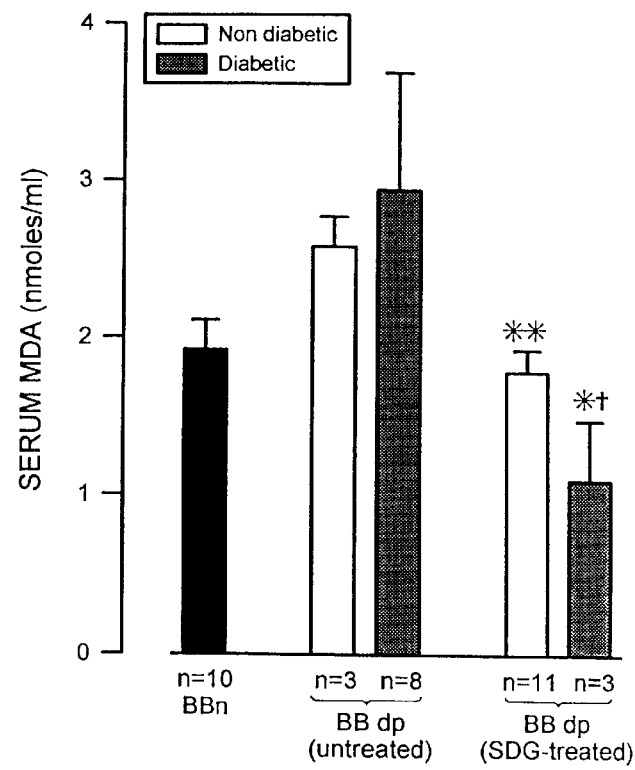
FIG. 3 is a bar graph showing serum MDA levels in three experimental groups.

FIG. 3. shows the serum MDA levels in the three experimental groups, with the results being expressed as mean±SE.

*$p<0.05$, different from BBn control.

**$p<0.05$, comparison between nondiabetic.

†$p<0.05$, different from nondiabetic rats within each treatment.

Figure 4:
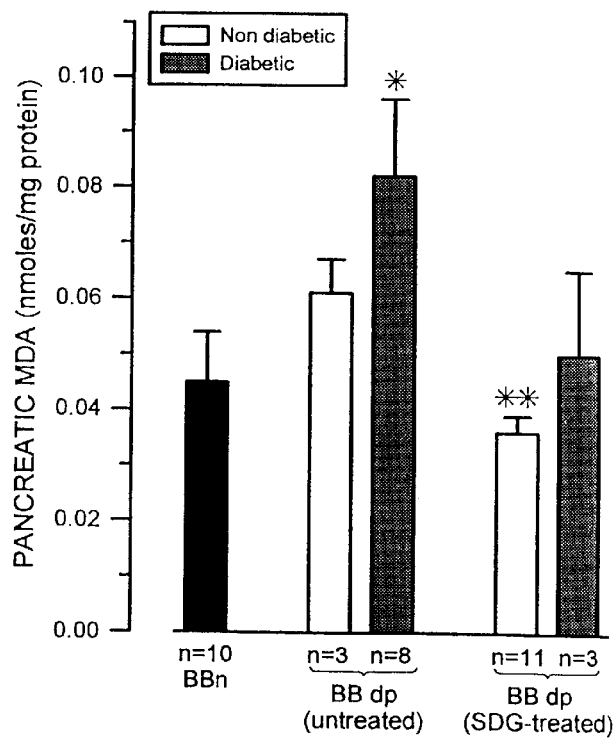
FIG. 4 is a bar graph showing pancreatic MDA levels in three experimental groups.

FIG. 4 shows the pancreatic-MDA levels in the three experimental groups, with the results being expressed as mean±SE.

*$p<0.05$, different from BBn control group.

**$p<0.05$, different from nondiabetic rats in the untreated group.

Figure 5:
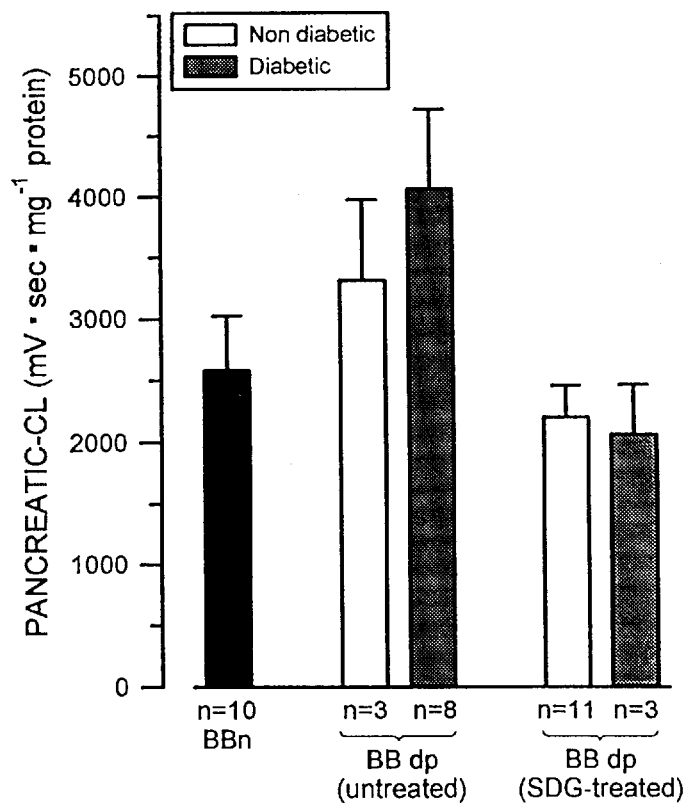
FIG. 5 is a bar graph showing pancreatic-chemiluminescence in three experimental groups.

FIG. 5 shows the pancreatic-chemiluminescence (Pancreatic-CL), a measure of antioxidant reserve. High Pancreatic-CL means decreased antioxidant reserve and vice-versa. Results are expressed as mean±SE.

None of the BBn (control) rats developed diabetes mellitus (glucosuria) and serum glucose was 7.24±0.48 mmoles/L. It was found that 72.7% of the untreated BBdp rats developed diabetes and serum glucose was markedly elevated as compared to those that did not develop diabetes (FIGS. 1–2). Only 21.4% of SDG-treated BBdp rats developed diabetes and serum glucose was higher than those not developing diabetes in this group. SDG treatment prevented the development of diabetes by 70.55%. It also delayed the onset of diabetes in ones that developed diabetes. The rats in BBdp groups that did not develop diabetes had serum glucose levels similar to the control (BBn) group. Serum and pancreatic MDA increased in BBdp untreated rats that developed diabetes but values were significant in pancreatic MDA only. Pancreatic serum MDA were lower in the SDG-treated group in both nondiabetic and diabetic as compared to untreated BBdp rats (FIGS. 3–4). Pancreatic antioxidant reserve was slightly lower in the untreated group as compared to the control or SDG-treated group but were not significant (FIG. 5).

These results indicate that SDG prevented the development of diabetes in BBdp rats by 70.55% and delayed the onset of the symptoms.

NIDDM (Type II Diabetes Mellitus)

This study was designed to investigate if SDG could reduce the incidence or delay the onset of diabetes (glucosuria) of NIDDM in the Zucker diabetic fatty rat (ZDF) a model of spontaneous NIDDM, and if NIDDM is associated with oxidative stress. Oxidative stress was assessed by measuring lipid peroxidation product malondialdehyde (MDA) a measure of levels of oxygen radicals, and tissue chemiluminescence (CL) an index of antioxidant reserve in blood and pancreatic tissue. Male 5–6 weeks old ZDF and age match Zucker lean control (ZLC) rats were obtained from Charles River, St. Constant, Quebec, Canada.

Rats were tested for glucosuria to establish diabetes at 5–6 weeks before they were assigned to various groups. None of the rats had glucosuria at this age. Group I, ZDF rats 5–6 weeks of age before onset of diabetes (n=4); Group II, ZDF rats maintained for 12 weeks (n=10); Group III, ZDF rats receiving SDG (22 mg/kg, daily orally in drinking water) until they achieve an age of 12 weeks (n=10); Group IV, ZLC rats sacrificed at 6 weeks of age (n=4); Group V, ZLC rats sacrificed at 12 weeks of age. At the end of the protocol, under anesthesia, blood samples were taken to measure serum glucose and MDA, and pancreas were removed to assess pancreatic MDA and antioxidant reserve.

None of the rats had diabetes (glucosuria) at the age of 5–6 weeks, However, the serum glucose in Group I was higher than in Group IV at the age of 5–6 weeks. In specific examinations of two rats that had not received SDG and two rats that had received SDG, the two rats that had not received SDG showed clear signs of diabetes while the two rats that had received SDG showed no signs of diabetes.

I claim:

1. A method for treating hypercholesterolemic atherosclerosis or for reducing total cholesterol which comprises administering to a patient an effective amount of secoisolariciresinol diglucoside (SDG) having a purity of at least 85%.

2. A method according to claim 1 wherein the SDG is obtained from flaxseed.

3. A method according to claim 1 wherein the SDG has a purity of at least 95%.

4. A method according to claim 1 wherein the SDG is administered in an amount of 5–20 mg per kg of body weight.

5. A method according to claim 1 wherein the SDG has a purity of at least 90%.

6. A method for reducing total cholesterol which comprises administering to a patient an effective amount of secoisolariciresinol diglucoside (SDG) having a purity of at least 95%.

7. A method for treating hypercholesterolemic atherosclerosis which comprises administering to a patient an effective amount of secoisolariciresinol diglucoside (SDG) having a purity of at least 95%.

8. A method for the treatment of diabetes mellitus which comprises administering to a patient an effective amount of secoisolariciresinol diglucoside (SDG) having a purity of at least 85%.

9. A method according to claim 8 wherein the SDG is obtained from flaxseed.

10. A method according to claim 9 wherein the SDG has a purity of at least 95%.

11. A method according to claim 10 wherein the SDG is administered in an amount 5–20 mg per kg of body weight.

12. A method according to claim 8 wherein the SDG has a purity of at least 90%.

* * * * *